(12) United States Patent
Shalaby et al.

(10) Patent No.: US 7,264,822 B2
(45) Date of Patent: Sep. 4, 2007

(54) CONJUGATED DRUG-POLYMER COATED STENT

(75) Inventors: Shalaby W. Shalaby, Anderson, SC (US); Todd Campbell, Petaluma, CA (US)

(73) Assignee: Poly-Med, Inc., Anderson, SC (US)

( * ) Notice: Subject to any disclaimer, the term of this patent is extended or adjusted under 35 U.S.C. 154(b) by 425 days.

(21) Appl. No.: 10/116,458

(22) Filed: Apr. 3, 2002

(65) Prior Publication Data

US 2003/0190341 A1    Oct. 9, 2003

(51) Int. Cl.
- *A61F 2/00* (2006.01)
- *A61K 31/34* (2006.01)
- *A61K 31/335* (2006.01)
- *A61M 31/00* (2006.01)

(52) U.S. Cl. .................. 424/423; 514/461; 514/463; 514/467; 604/500

(58) Field of Classification Search ............... 424/422, 424/423, 426; 514/2, 27, 283, 291, 44, 54; 604/500
See application file for complete search history.

(56) References Cited

U.S. PATENT DOCUMENTS

| | | | |
|---|---|---|---|
| 3,755,558 A | 8/1973 | Scribner | |
| 3,773,919 A | 11/1973 | Boswell et al. | |
| 4,328,204 A | 5/1982 | Wasserman et al. | |
| 5,654,381 A | 8/1997 | Hrkach et al. | |
| 5,800,541 A * | 9/1998 | Rhee et al. ................ | 424/423 |
| 6,051,576 A | 4/2000 | Ashton et al. | |
| 6,262,107 B1 * | 7/2001 | Li et al. ..................... | 514/449 |
| 6,273,913 B1 * | 8/2001 | Wright et al. .............. | 623/1.42 |
| 2003/0129215 A1 * | 7/2003 | Mollison et al. ........... | 424/426 |
| 2003/0170286 A1 * | 9/2003 | Ashton et al. .............. | 424/423 |
| 2003/0199964 A1 * | 10/2003 | Shalaby et al. ............ | 623/1.11 |

FOREIGN PATENT DOCUMENTS

| | | | |
|---|---|---|---|
| EP | 0 879 595 | * | 11/1998 |
| EP | 0879595 A2 | | 11/1998 |
| WO | WO99/30684 | * | 6/1999 |
| WO | WO02087586 A1 | | 11/2002 |

\* cited by examiner

*Primary Examiner*—Michael G. Hartley
*Assistant Examiner*—Blessing Fubara

(57) ABSTRACT

One aspect of the invention is a system for treating vascular conditions, including a catheter, a stent coupled to the catheter, and a polymeric coating on the stent comprising at least one conjugated drug. Each conjugated drug includes a control agent and a bioactive agent, where the control agent controls the elution rate of the bioactive agent.

23 Claims, 5 Drawing Sheets

CONJUGATED DRUG-POLYMER COATED STENT

FIELD OF THE INVENTION

This invention relates generally to medical devices. More specifically, the invention relates to a conjugated drug-polymer coating on a stent for in vivo, timed-release drug delivery.

BACKGROUND OF THE INVENTION

Cardiovascular and lumenal stents are highly effective in the treatment of heart disease and other vascular conditions by the dilation and retention of constricted vessels or bodily conduits. However, their insertion may induce undesirable bodily reactions such as inflammation, infections, thrombosis or blood clots, restenosis, and proliferation of cell growth that occludes the passageway and may incur the need for additional surgery. Pharmaceutical drugs and compounds may assist in preventing these conditions, although they may be required in large oral or intravenous doses with stringent intake or injection timetables to increase their efficacy.

Pharmaceutical compounds may be coated directly on the stent to provide a preferable point-of-use drug delivery system, but these coatings must be bioengineered to control the release of sometimes highly potent and potentially toxic drugs. Timed-release attributes of a coating must be incorporated to avoid clinically unacceptable premature releases of toxic levels of potent drugs. Biocompatible, biodegradable polymers for various biomedical applications such as those used in sutures and tissue engineering have been described in "Functionalized Polyester Graft Copolymers," Hrkach, et al., U.S. Pat. No. 5,654,381, issued Aug. 5, 1997. Drug-polymers based on polylactide and drug mixtures in particle or pellet form to provide timed-release delivery are described in "Polylactide-Drug Mixtures," Boswell, et al., U.S. Pat. No. 3,773,919, issued Nov. 20, 1973, or in a spray form as described in "Polylactide-Drug Mixtures for Topical Application," Scribner, et al., U.S. Pat. No. 3,755,558, issued Aug. 28, 1973. Reducing the water solubility of pharmaceutical compounds has been recognized as a technique for enhancing timed-release attributes of the compounds. A composition for administration of a paclitaxel derivative with a water solubility less than that of paclitaxel and its incorporation into a suitable polymeric carrier including a stent formed from the polymer has been described in "Composition and Methods for Administration of Water-insoluble Paclitaxel Derivatives," Alvarado, et al., international publication number WO 00/41687, published Jul. 20, 2000. Drugs contained within a polymeric matrix for inhibiting stenosis following vascular trauma are presented in "Therapeutic Inhibitor of Vascular Smooth Muscle Cells," L. Kunz, international publication number WO 94/07529, published Apr. 14, 1994. A polymeric coating on a stent including two layers, the outer layer being a surface erodable polymer and an inner layer including a drug, is described in "Stents Having Multiple Layers of Biodegradable Polymeric Composition," Wang, et al, international publication number WO 98/56312, published Dec. 17, 1998.

These developments in pharmaceutical coatings, however, have limited control over the delivery of the drug and versatility in the types of drugs to be delivered and their pharmacodynamics. The delivery of the drug may be too fast, ineffective and possibly toxic, or too slow and ineffective. The drug coating may not stick or adhere. The drug polymer coatings should coat the stent framework without cracking, peeling or delaminating, particularly when the stent is expanded during installation. The coating should not fall off, crack, fracture, crystallize or melt during processing, sterilizing, or installing. In some cases, a rapid delivery of a drug may be needed immediately following surgery, followed by a steady delivery of the drug at a lesser rate over an extended period of time. Because there is need for the in vivo delivery of more than one drug, delivery of one or multiple drug types from a deployed, coated stent with variable elution rates is desirable. One drug type in a polymer coating may elute faster than another drug type in the same polymer, thus methods of modulating a drug without impacting its bioactive moiety are desirable.

An object of the current invention is to tailor a bioactive agent such as a drug in a pharmacologically unaltered way for controlled delivery from a stent coating, and to provide a drug-polymer system that can be tailored to the desired elution rate for a specific bioactive agent. Another objective is to modulate a bioactive agent and interdisperse the bioactive agent within a polymer matrix for controlled delivery from the stent coating. Another objective is to modify a polymer coating with a bioactive agent or pharmaceutical drug and coat the stent for controlled, timed release from the stent. Another objective is to provide a robust stent coating to survive expansion of the stent, whether by balloon expansion or by self-expansion. Another object is to provide a means for drug delivery from an endovascular stent with desired, timed-release properties.

It is a further object of this invention, therefore, to provide a method and system for treating heart disease, cardiovascular ailments and other vascular conditions utilizing catheter-delivered stents, as well as overcome the obstacles described above.

SUMMARY OF THE INVENTION

One aspect of the current invention is a system for treating a vascular condition including a catheter, a stent coupled to the catheter, and a polymeric coating on the stent comprising at least one conjugated drug. Each conjugated drug may include a control agent and a bioactive agent, where the control agent controls the elution rate of the bioactive agent.

The catheter may include a balloon used to expand the stent, or a sheath that retracts to allow expansion of the stent.

The bioactive agent may include an antineoplastic agent, an antiproliferative agent, an antibiotic, an anti-inflammatory agent, an organic drug, a pharmaceutical compound, a recombinant DNA product, a recombinant RNA product, a collagen, a collagenic derivative, a protein, a protein analog, a saccharide, or a saccharide derivative. The bioactive agent may include podophyllotoxin, etoposide, camptothecin, a camptothecin analog, mitoxantrone, rapamycin, and their derivatives. The bioactive agent may control cellular proliferation.

The polymeric coating may erode from the stent to elute at least one bioactive agent. The polymeric coating may include a polymeric matrix, where at least one conjugated drug is dispersed within the matrix, and where the conjugated drug diffuses from the polymeric matrix to elute the bioactive agent. The polymeric matrix may be comprised of a caprolactone polymer. The bioactive agent may separate from the control agent when the bioactive agent is eluted from the polymeric coating.

The control agent may be covalently linked to the bioactive agent. The covalently linked control agent may include at least one polyester chain. The polyester chain may be linked to the bioactive agent with an ester group. The covalently linked control agent may be derived from at least one cyclic monomer. The cyclic monomer may include lactide, glycolide, p-dioxanone, e-caprolactone, trimethylene carbonate, or 1,5-dioxepan-2-one.

The conjugated drug may include a pseudodimer of the bioactive agent, with a molecular weight of the pseudodimer at least twice that of the bioactive agent. The pseudodimer may include a first bioactive agent and a second bioactive agent connected by a pseudodimeric interlinking group. The pseudodimeric interlinking group may include a hydrolabile ester bridge, an oxalate group, or a carbonate group. The first bioactive agent may be a molecule of podophyllotoxin, the second molecule may be a second molecule of podophyllotoxin, and the pseudodimeric interlinking group may comprise an oxalate bridge. The first bioactive agent may be phyllotoxin, the second bioactive agent may also be phyllotoxin, and the pseudodimeric interlinking group may comprise a carbonate bridge.

The conjugated drug may include a pseudo-oligomer of the bioactive agent, where the pseudo-oligomer has a molecular weight of at least three times that of the bioactive agent.

The bioactive agent may include a lipophilic drug derivative of a lipophilic drug, where the molecular weight of the conjugated drug has a molecular weight greater than that of the lipophilic drug derivative. The lipophilic drug derivative may include a non-pharmacologically critical hydroxyl group. The control agent may be attached to the non-pharmacologically critical hydroxyl group. The control agent may include an acid chloride. The lipophilic drug may include podophyllotoxin and the control agent may include an acid anhydride of a fatty acid with between three and twenty carbon atoms. The acid anhydride may be a stearic acid anhydride. The lipophilic drug derivative may include a non-pharmacologically critical lactone. The lipophilic drug may be podophyllotoxin and the control agent may include a long-chain fatty acid with between three and twenty carbon atoms.

Another aspect of the current invention is a drug-polymer coated stent, including a cardiovascular stent with a stent framework and a polymeric coating on the stent framework, where the polymeric coating includes a biocompatible polymer with an interdispersed conjugated drug, and where the elution rate of the interdispersed conjugated drug is predetermined.

Another aspect of the current invention is a drug-polymer coated stent, including a cardiovascular stent with a stent framework and a polymeric coating on the stent framework, where the polymeric coating includes a conjugated drug, and where the elution rate of the conjugated drug may be predetermined.

Another aspect of the current invention is a method of manufacturing a drug-polymer coated stent, including the steps of providing a stent framework, forming a conjugated drug where the conjugated drug comprises a bioactive agent and a control agent, and coating the stent framework with the conjugated drug. The conjugated drug may include a covalently-linked conjugated drug, a pseudodimeric conjugated drug, a pseudo-oligomeric conjugated drug, and a lipophilic conjugated drug.

The conjugated drug may be formed by mixing a bioactive agent and at least one monomer in a solution, adding a catalyst to the solution, and forming a covalently-linked conjugated drug, where an absorbable polyester chain is linked to the bioactive agent, and the bioactive serves as a chain initiator. The bioactive agent may be podophyllotoxin, the monomer may be a mixture of e-caprolatone and glycolide, and the catalyst may be stannous octoate. The bioactive agent may be podophyllotoxin, the monomer may be a mixture of e-caprolatone and glycolide, and the catalyst may be a zinc dialkyl.

The conjugated drug may be formed by providing at least two molecules of a hydroxylic bioactive agent, mixing the molecules of the hydroxylic bioactive agent with at least one molecule of a pseudodimeric interlinking group in a solution, adding a pseudodimerization catalyst to the solution, heating the solution to a pseudodimeric reaction temperature, and forming a pseudodimeric conjugated drug where a first molecule of the bioactive agent is connected to a second molecule of the bioactive agent by a molecule of the pseudodimeric interlinking group. The pseudodimeric interlinking group may include diethyl oxalate. The pseudodimeric interlinking group may include di-isopropyl carbonate. The pseudodimerization catalyst may include an organometallic transesterification catalyst. The solution may include a non-reactive solvent, and the pseudodimerization reaction temperature may be between 25 degrees and 140 degrees centigrade.

The conjugated drug may be formed by providing at least three molecules of a hydroxylic bioactive agent, mixing at least three molecules of the hydroxylic bioactive agent and at least two molecules of a pseudo-oligomeric interlinking group in a solution, adding a pseudo-oligomerization catalyst to the solution, heating the solution to a pseudo-oligomeric reaction temperature, and forming a pseudo-oligomeric conjugated drug where a first molecule of the bioactive agent may be connected to a second molecule of the bioactive agent by a first molecule of the pseudo-oligomeric interlinking group, and the second molecule of the bioactive agent may be connected to a third molecule of the bioactive agent by a second molecule of the pseudo-oligomeric interlinking group. The pseudo-oligomerization reaction temperature may be between 25 degrees and 140 degrees centigrade.

The conjugated drug may be formed by providing a bioactive agent with a non-pharmacologically critical hydroxyl group, mixing the bioactive agent with an acid chloride in a solution, heating the solution to a lipophilic reaction temperature, and forming a lipophilic conjugated drug. The bioactive agent may be podophyllotoxin. The lipophilic reaction temperature may be between 25 degrees and 140 degrees centigrade.

The conjugated drug may be formed by providing a bioactive agent with a non-pharmacologically critical hydroxyl group, mixing the bioactive agent with an acid anhydride of a fatty acid comprising between three and twenty carbon atoms in a solution, heating the solution to a lipophilic reaction temperature, and forming a lipophilic conjugated drug. The bioactive agent may be podophyllotoxin. The lipophilic reaction temperature may be between 25 degrees and 140 degrees centigrade.

The conjugated drug may be formed by providing a bioactive agent with a non-pharmacologically critical lactone, mixing the bioactive agent with a long-chain fatty alcohol with between three and twenty carbon atoms in a solution, adding a lipophilic catalyst to the solution, heating the solution to a lipophilic reaction temperature, and forming a lipophilic conjugated drug. The bioactive agent may be podophyllotoxin. The lipophilic catalyst may be an organometallic transesterification catalyst. The lipophilic reaction temperature may be between 25 degrees and 140 degrees centigrade.

A polymer coating material may be mixed with the conjugated drug prior to coating the stent framework. The polymeric coating material may include polycaprolactone, a caprolactone copolymer, a synthetic polymer, a naturally occurring polymer, a non-synthetic polymer derivative, or any suitable polymer coating material.

The stent framework may include a metallic or polymeric base.

Another aspect of the current invention is a method for treating vascular conditions, including the steps of inserting a stent within a vessel in a body, separating at least a portion of a polymeric coating on the stent into a bioactive agent and a control agent, and eluting the bioactive agent. The control agent may control the elution rate of the bioactive agent. The control agent may be selected based on a predetermined elution rate of the bioactive agent.

Another aspect of the current invention is a system for treating a vascular condition, including a means for inserting a stent within a vessel in a body, a means for allowing separation of at least a portion of a polymeric coating on the stent into a bioactive agent and a control agent, and a means for eluting the bioactive agent.

The aforementioned, and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 1:
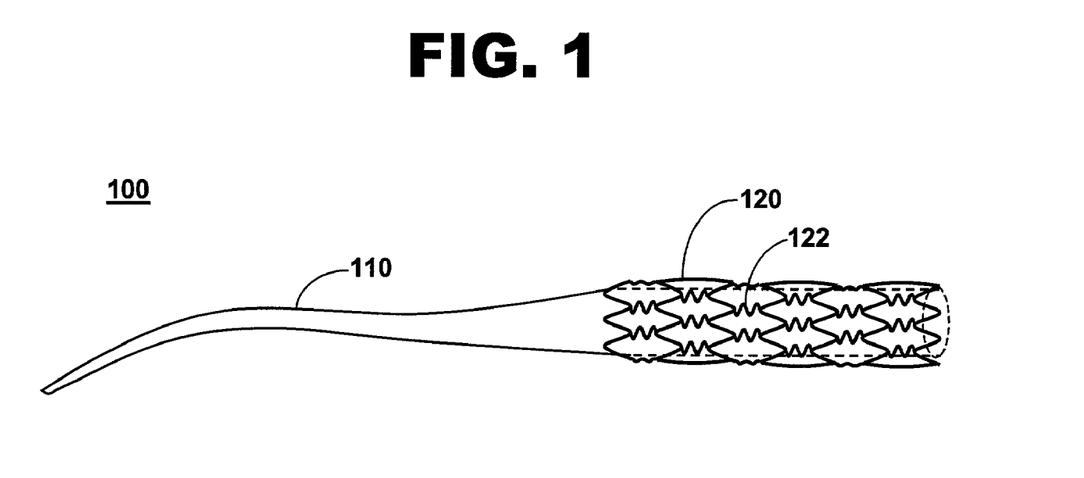
FIG. 1 is an illustration of one embodiment of a system for treating vascular conditions containing a catheter, a stent, and a drug-polymer coating the stent, in accordance with the current invention.

One aspect of the present invention is a system for treating coronary heart disease and other vascular conditions, using catheter-deployed endovascular stents with polymeric coatings including one or more modulated drugs with desired timed-release properties. Treatment of vascular conditions may include the prevention or correction of various ailments and deficiencies associated with the cardiovascular system, urinogenital systems, biliary conduits, abdominal passageways and other biological vessels within the body. One embodiment of the system for treating vascular conditions, in accordance with the present invention, is illustrated in FIG. 1 at 100. Vascular condition treatment system 100 may include a catheter 110, a stent 120 coupled to the catheter, and a polymeric coating 122 on the stent or stent framework. Polymeric coating 122 may include one or more conjugated drugs. A conjugated drug may include a control agent and a bioactive agent. The bioactive agent may be a pharmacologically active drug or bioactive compound. The bioactive agent may be a collagen, a collagenic derivative, a protein, or a protein analog. The bioactive agent may be a saccharide, polysaccharide, or a saccharide derivative. The bioactive agent may be any pharmacologically beneficial or therapeutic material. The control agent may control the elution rate of the bioactive agent. Elution refers to the transfer of the bioactive agent out from polymeric coating 122. The elution rate is determined by the rate at which the bioactive agent is excreted from polymeric coating 122 into the body, typically measured in weight per unit time, or in weight per unit time per peripheral area of the stent.

Control of the elution rate of the bioactive agent may be achieved by increasing the effective molecular weight of the bioactive agent and thereby slowing the diffusion of the conjugated drug from the polymeric coating; by decreasing the effective solubility of the bioactive agent in the body with the addition of less soluble attachments; by providing linkages such that the bioactive agent may have an increased affinity for the polymeric coating with the concomitant tendency to reside within the polymeric coating for longer periods of time; by attaching slowly hydrolyzable molecular extensions for decreasing the absorption rate into the biomaterial adjacent the stent coating; by adding attachments that slow the metabolization of the bioactive agent; or any combination of the above.

Upon insertion of catheter 110 and stent 120 with polymeric coating 122 into a directed vascular region of a human body, stent 120 may be expanded by applying pressure to a suitable balloon inside the stent, or by retracting a sheath to allow expansion of a self-expanding stent. Balloon deployment of stents and self-expanding stents are well known in the art. Catheter 110 may include the balloon used to expand stent 120. Catheter 110 may include a sheath that retracts to allow expansion of the stent.

Another aspect of the current invention is a drug-polymer coated stent with a stent framework and a polymeric coating on the stent framework. The polymeric coating may include one or more conjugated drugs, each with a predetermined elution rate. Non-conjugated drugs and bioactive agents may also be included in the polymeric coating.

Figure 2:
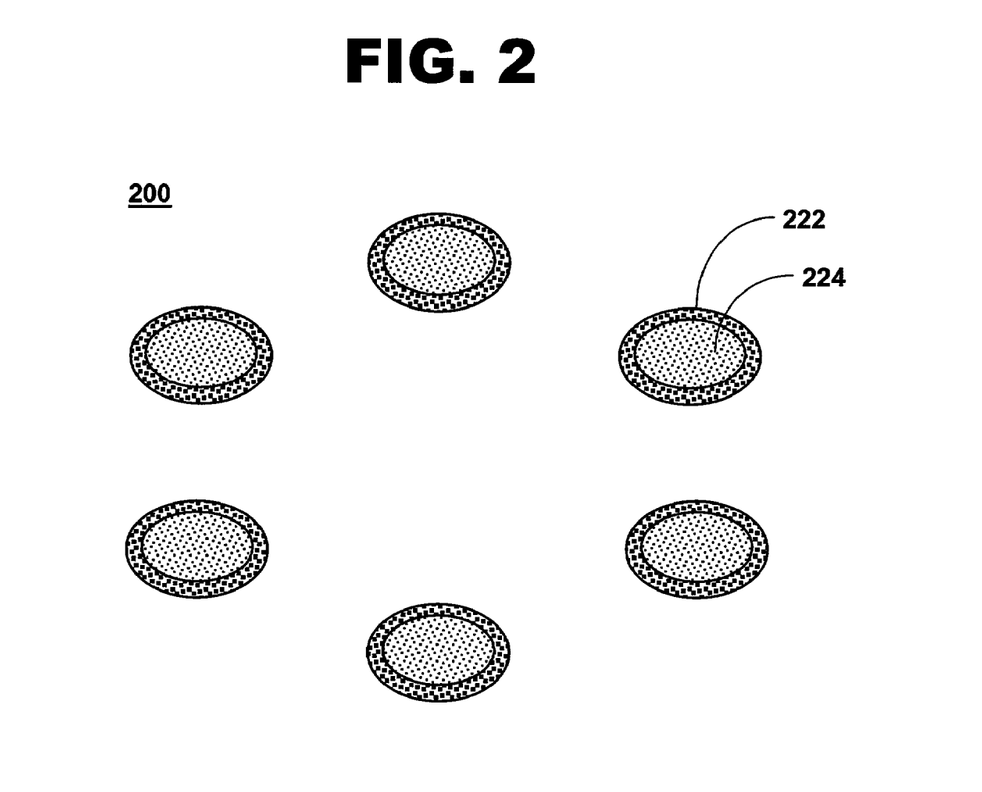
FIG. 2 is an illustration of a stent cross-section containing a drug-polymer coating the stent surface, in accordance with the current invention.

FIG. 2 shows an illustration of a stent cross-section containing a drug-polymer coating on the stent surface, in accordance with the present invention at 200. Drug-polymer coated stent 200 may include a polymeric coating 222 on a stent framework 224. Polymeric coating 222 may contain one or more conjugated drugs. Polymeric coating 222 may contain a polymeric matrix in which one or more conjugated drugs are interdispersed. Stent framework 224 may include a metallic or polymeric base. Stent framework 224 may include a metallic base such as stainless steel or nitinol, a polymeric base, a drug-polymer base, or any suitable, biocompatible base material.

The bioactive agent may include an antineoplastic agent such as triethylene thiophosphoramide, an antiproliferative agent, an antibiotic, an anti-inflammatory agent, an organic drug, a pharmaceutical compound, a recombinant DNA product, a recombinant RNA product, a collagen, a collagenic derivative, a protein, a protein analog, a saccharide, or a saccharide derivative. An antineoplastic agent may prevent, kill, or block the growth and spread of cancer cells in the vicinity of the stent. An antiproliferative agent may prevent or stop cells from growing. An antibiotic may kill or inhibit the growth of microorganisms and may be used to combat disease and infection. An anti-inflammatory agent may be used to counteract or reduce inflammation in the vicinity of the stent. An organic drug may be any small-molecule therapeutic material. A pharmaceutical compound may be any compound that provides a therapeutic effect. A recombinant DNA product or a recombinant RNA product may include altered DNA or RNA genetic material. For example, the bioactive agent may be selected to inhibit vascular restenosis, a condition corresponding to a narrowing or constriction of the diameter of the bodily lumen where the stent is placed. The bioactive agent may generally control cellular proliferation. The control of cell proliferation may include enhancing or inhibiting the growth of targeted cells or cell types.

The bioactive agent may include podophyllotoxin, etoposide, camptothecin, a camptothecin analog, mitoxantrone, rapamycin, and their derivatives or analogs. Podophyllotoxin is an organic, highly toxic drug that has antitumor properties and may inhibit DNA synthesis. Etoposide is an antineoplastic that may be derived from a semi-synthetic form of podophyllotoxin to treat monocystic leukemia, lymphoma, small-cell lung cancer, and testicular cancer. Camptothecin is an anticancer drug that may function as a topoisomerase inhibitor. Related in structure to camptothecin, a camptothecin analog such as aminocamptothecin may be used as an anticancer drug. Mitoxantrone is also an important anticancer drug, used to treat leukemia, lymphoma, and breast cancer. Rapamycin or sirolimus is a medication that may interfere with the normal cell growth cycle and may be used to reduce restenosis. The bioactive agent may also include analogs and derivatives of these agents.

Polymeric coating 122, 222 may soften, dissolve or erode from the stent to elute at least one bioactive agent. This elution mechanism may be referred to as surface erosion where the outside surface of the polymeric coating dissolves, degrades, or is absorbed by the body; or bulk erosion where the bulk of the polymeric coating biodegrades to release the bioactive agent. Eroded portions of the polymeric coating may be absorbed by the body, metabolized, or otherwise expelled.

The conjugated drug may separate within polymeric coating 122, 222 and elute the bioactive agent. Alternatively, the conjugated drug may erode from stent 120 and then separate into the non-pharmacologically active control agent and the bioactive agent. The control agent may be absorbed or expelled by the body, or further degraded and absorbed or expelled. Polymeric coating 122, 222 may include multiple conjugated drugs, each with a bioactive agent and control agent selected to provide a predetermined elution rate. Polymeric coating 122, 222 may include a single bioactive agent with various control agents to control the physical properties and the elution rates of the bioactive agent.

Polymeric coating 122, 222 may also include a polymeric matrix. For example, the polymeric matrix may include a caprolactone-based polymer or copolymer, or various cyclic polymers. The polymeric matrix may include various synthetic and non-synthetic or naturally occurring macromolecules and their derivatives. The conjugated drug may be dispersed throughout the polymeric matrix. The conjugated drug or the bioactive agent may diffuse out from the polymeric matrix to elute the bioactive agent. The conjugated drug may diffuse out from the polymeric matrix and into the biomaterial surrounding the stent, and separate into the bioactive agent and the control agent to elute the bioactive agent. The control agent may be metabolized or expelled from the body. The bioactive agent may separate from the control agent within polymeric coating 122, 222 and diffuse out from the polymeric matrix into the surrounding biomaterial.

The control agent may be selected to provide a desired elution rate of the bioactive agent. The conjugated drugs may be synthesized such that a particular bioactive agent may have two different elution rates by selecting different control agents. A bioactive agent with two different elution rates, for example, would allow rapid delivery of the pharmacologically active drug within twenty-four hours of surgery, with a slower, steady delivery of the drug, for example, over the next six to twelve months.

Figure 3:
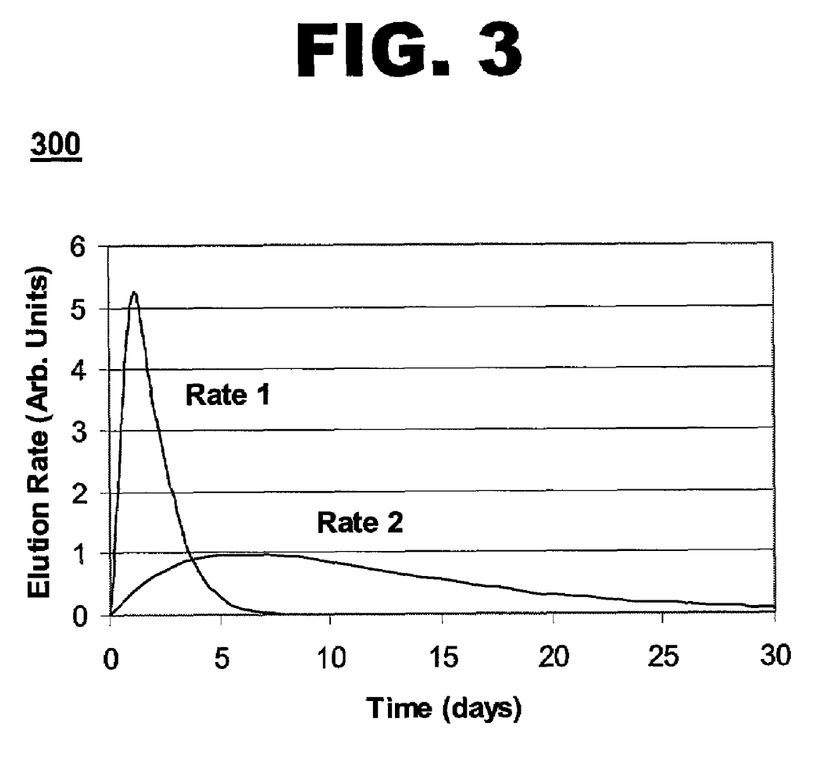
FIG. 3 is a graphical illustration of elution rates for a drug-polymer coated stent, in accordance with the current invention.

FIG. 3 shows a graphical illustration of elution rates for a drug-polymer coated stent, in accordance with the present invention at 300. Elution rate graph 300 shows the rate at which a bioactive agent may elute from a drug-polymer coated stent for two different predetermined rates. The elution rate of the bioactive drug is indicated with arbitrary units. Typical units used for drug elution rates include micrograms per hour, day or month, or may be normalized to a unit volume with units such as micrograms per day per cubic centimeter of drug-polymer, or may be normalized to the periphery area of the stent. Drug elution may be expressed in total milligrams or micrograms eluted from the drug-polymer, or as a fractional percentage of the initial drug weight at particular points in time. Rate 1 of elution rate graph 300 shows a high rate of drug delivery over a shorter interval of time such as minutes or hours, whereas Rate 2 of elution rate graph 300 shows a slower rate of drug delivery over a longer period of time, such as days, weeks or months. The elution rate of the bioactive agent may be established by the selection of the control agent, the method of preparation of the conjugated drug, and the optional use of a polymeric matrix in the drug-polymer coating.

The control agent may be covalently linked to the bioactive agent. Modulating the physical properties and bioavailability of bioactive agents without altering their pharmacological effects using covalent linking of the bioactive agents and polymeric chains has been limited to polyethylene glycol (PEG) as the preferred polymer. And, in most cases, PEG may be linked covalently to complex proteins and other biomolecules to increase their biostability and, hence, increase their in vivo residence time. Linking the PEG to the bioactive agent, in practically all cases, has been achieved through the establishment of an ester linkage with the premise that the water-soluble PEG will be released by hydrolysis as the modified drug is metabolized. Unfortunately, drug modulation using PEG can be affected by only the molecular weight of the hydrophilic PEG chain. Such an approach to drug modulation limits the versatility of drug covalent conjugation with other types of polymeric chains, which are capable of imparting a broad range of properties to any specific drug.

Another aspect of the present invention includes novel forms of linking bioactive agents, including simple organic drugs to longer polymer chains other than PEG, in order to control the release of pharmaceutically active drugs from polymeric coating 122, 222. Accordingly, one aspect of the invention presents potent organic drugs that are covalently linked to absorbable chains that can be disassociated from the drug at once, or incrementally, to release bioactive agents and biodegradable by-products.

Figure 4:
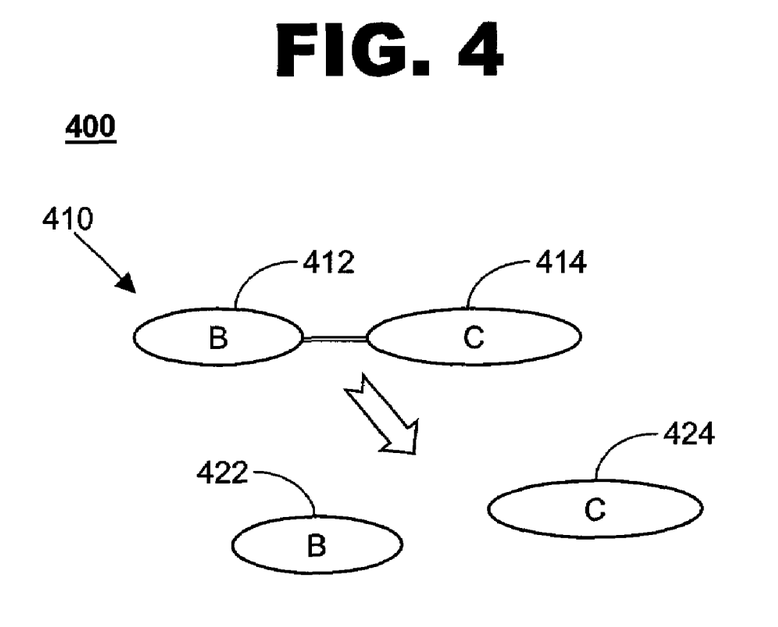
FIG. 4 is a schematic diagram of a covalently-linked conjugated drug and its timed-release mechanism, in accordance with the current invention.

The control agent of a covalently-linked conjugated drug may include one or more polyester chains. FIG. 4 shows a schematic diagram of a covalently-linked conjugated drug and its timed-release mechanism, in accordance with the present invention at 400. Covalently-linked conjugated drug 410 may include a bioactive agent 412 covalently coupled or linked to control agent 414. The polyester chain may be linked to the bioactive agent with an ester group. The polyester chain may be derived from one or more cyclic monomers. The cyclic monomer may include lactide, glucolide, p-dioxanone, e-caprolactone, trimethylene carbonate, and 1,5-dioxepan-2-one.

The covalently-linked conjugated drug may be formed by mixing a bioactive agent and one or more monomers in a solution, adding a catalyst to the solution, and forming a covalently linked conjugated drug where an absorbable polyester chain may be covalently linked to the bioactive agent, and where the bioactive agent may serve as the chain initiator. The bioactive agent may be podophyllotoxin, the monomer may be a mixture of e-caprolactone and glycolide, and the catalyst may be stannous oxide or a zinc alkyl. The catalyst may be any other organometallic compound, such as diethyl, dimethyl or dibutyl aluminum, that accelerates the ring opening polymerization and linking of the monomers onto the bioactive agent. The solution may be a mixture including a molten monomer or a mixture of molten monomers. The solution may include an inert organic liquid. The solution may contain an organic solvent.

Covalently-linked conjugated drug 410 may separate after a time from stent 120, 220 deployment into bioactive agent 422 and control agent 424, allowing bioactive agent 422 to perform its intended pharmaceutical function, whereas control agent 424 may be retained within polymeric coating 122, 222, or may diffuse away from polymeric coating 122, 222 and expelled from the body or further degraded then expelled, or may be absorbed by the body in some pharmacologically benign form. Alternatively, bioactive agent 422 may exhibit pharmacodynamic behavior upon elution from stent 120, 220 without requiring separation from control agent 424.

The use of polymeric matrices to modulate the release of bioactive agents and their bioavailability in many controlled release systems allows maximization of the efficiency and a prolonging of the pharmacological effects of many drugs while minimizing, or eliminating, any potential toxicity that may be associated with single-dose administration. Among the major factors that control the release of a drug from a polymeric matrix are its molecular size (or molecular weight) and water solubility. For highly potent, small-size, moderately, or even slightly soluble drugs, modulating the release profile from polymeric matrices is a difficult task to achieve. The situation becomes even more complicated if the polymeric matrix is a thin coating, with a short free path for the drug to diffuse. The conjugated drug may include a pseudodimer of a bioactive agent. This novel approach increases drug size and decreases its solubility, without compromising its timely bioavailability in its active, free form. The molecular weight of the pseudodimeric conjugated drug may be between 200 and 60,000 Da, or larger.

A pseudodimer may be formed by two drug monomers by linking them at a non-pharmacologically significant point with a linking group. Formation of a pseudodimer of a drug increases the effective molecular weight of the drug without impacting its pharamcological moiety or bioavailability. In general, increasing the molecular weight decreases the water solubility of the bioactive agent. Increases in the molecular weight and decreases in water solubility provide mechanisms for delaying the elution of the modulated drug from the stent coating. Dispersion of the pseudodimeric conjugated drug throughout a polymeric matrix within the polymeric coating provides another mechanism for controlled release, as a larger molecular weight conjugated drug will generally exhibit slower diffusion from the coating.

Figure 5:
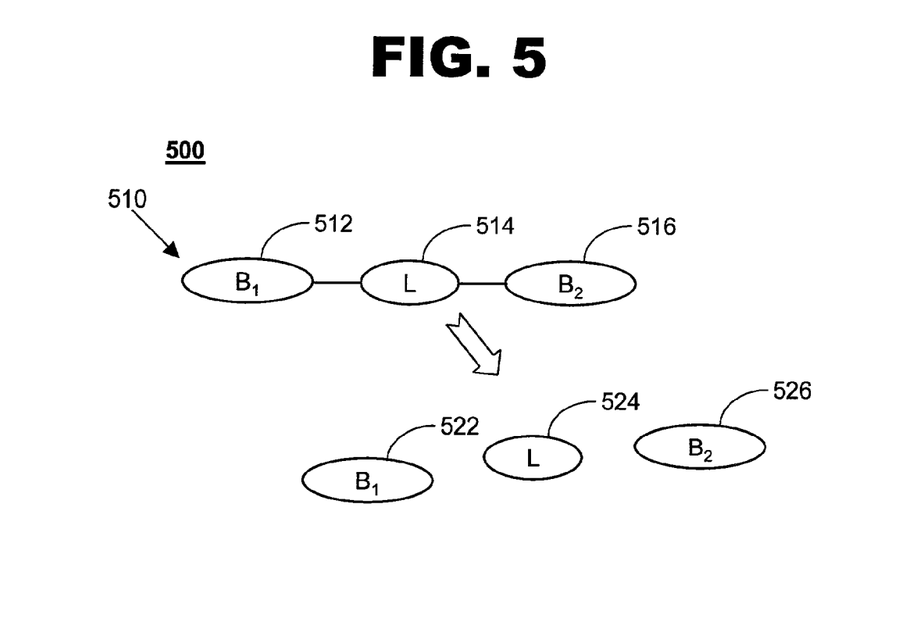
FIG. 5 is a schematic diagram of a pseudodimeric conjugated drug and its timed-release mechanism, in accordance with the current invention.

FIG. 5 shows a schematic diagram of a pseudodimeric conjugated drug and its timed-release mechanism, in accordance with the present invention at 500. Pseudodimeric conjugated drug 510 may include a first bioactive agent 512, a pseudodimeric interlinking agent or pseudodimeric interlinking group 514, and a second bioactive agent 516. Bioactive agent 512 and bioactive agent 516 may be the same, or different bioactive agents. Pseudodimeric conjugated drug 510 may have a molecular weight slightly more than double that of the bioactive agent when bioactive agent 512 and bioactive agent 516 are the same. Pseudodimeric conjugated drug 510 may have solubility in water less than that of the bioactive agent. Pseudodimeric conjugated drug 510 may include two monomers of the same bioactive agent connected by pseudodimeric interlinking group 514. The pseudodimeric interlinking group may serve as a pseudodimeric interlinking agent by enabling the linking of the two monomers.

Pseudodimeric conjugated drug 510 may include two different bioactive agents connected by pseudodimeric interlinking group 514. Pseudodimeric interlinking group 514 may include a hydrolabile ester bridge, an oxalate group, or a carbonate group. The first bioactive agent 512 may be a first molecule of podophyllotoxin, the second bioactive agent 516 may be a second molecule of podophyllotoxin, and the pseudodimeric interlinking group 514 may include an oxalate bridge or a carbonate bridge.

The pseudodimeric conjugated drug may be formed by providing at least two molecules of a hydroxylic bioactive agent. At least two molecules of the bioactive agent and at least one molecule of a pseudodimeric interlinking group may be mixed in a solution. The interlinking may be achieved using a pseudodimerization catalyst that may be added to the solution. The solution may be heated to a pseudodimerization reaction temperature, thereby forming the pseudodimeric conjugated drug where a molecule of the bioactive agent may be connected to a second molecule of the bioactive agent by a molecule of the pseudodimeric interlinking group. The pseudodimeric interlinking group may be diethyl oxalate, or di-isopropyl carbonate. The pseudodimerization catalyst may include an organometallic transesterification catalyst. The solution may include a nonreactive solvent. The pseudodimerization reaction temperature may be between 25 degrees and 140 degrees centigrade, preferably below 100 degrees centigrade, and even more preferably below 50 degrees centigrade.

After the deployment of stent 120, 220, pseudodimeric conjugated drug 510 may separate into bioactive agent 522, pseudodimeric interlinking group 524, and bioactive agent 526, allowing bioactive agents 522, 526 to perform their intended pharmaceutical function, while pseudodimeric interlinking group 524 may be retained within polymeric coating 122, 222, may be leeched from polymeric coating 122, 222 and expelled from the body or further degraded then expelled, or may be absorbed by the body in some pharmacologically benign form. Alternatively, bioactive agents 522, 526 may provide bioavailability upon elution from stent 120, 220 without requiring separation from pseudodimeric interlinking group 524.

Further increases in molecular weight and decreases in solubility with concomitantly controlled release attributes may be achieved by additional polymerization of a pseudodimeric conjugated drug. The conjugated drug may include a pseudo-oligomer of a bioactive agent.

Figure 6:
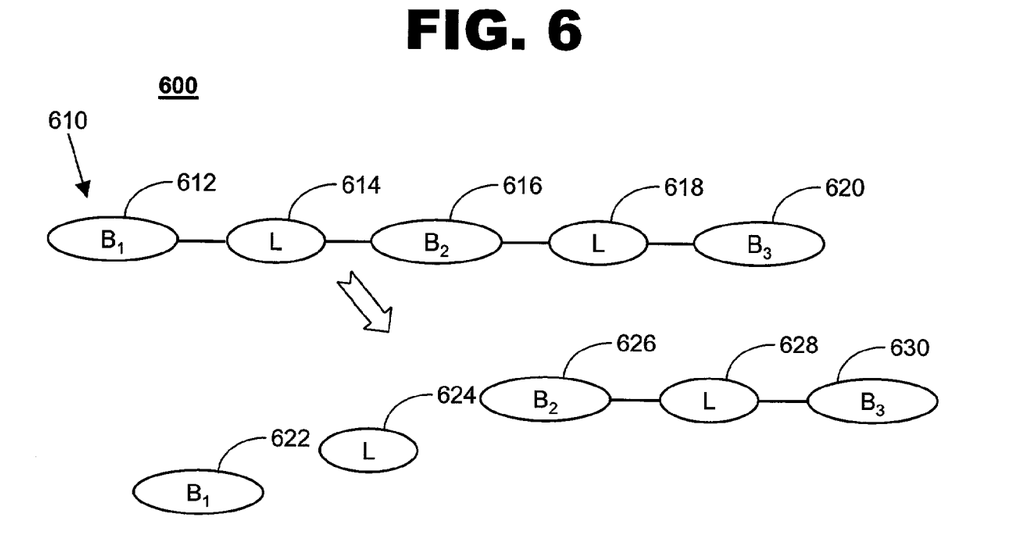
FIG. 6 is a schematic diagram of a pseudo-oligomeric conjugated drug and its timed-release mechanism, in accordance with the current invention.

FIG. 6 shows a schematic diagram of a pseudo-oligomeric conjugated drug and its timed-release mechanism, in accordance with the present invention at 600. Pseudo-oligomeric conjugated drug 610 may include a first bioactive agent 612, a first pseudo-oligomeric interlinking agent or first pseudo-oligomeric interlinking group 614, a second bioactive agent 616, a second pseudo-oligomeric interlinking agent or second pseudo-oligomeric interlinking group 618, and a third bioactive agent 620. Bioactive agents 612, 616, 620 may be the same type of bioactive agent, or different types of bioactive agents, or some combination thereof. Pseudo-oligomeric conjugated drug 610 may have a molecular weight at least three times greater than that of the bioactive agent. For instances where more than one bioactive agent comprises the pseudo-oligomeric conjugated drug, the molecular weight of the conjugated drug may be equal to or slightly more than the sum of the molecular weights of the individual bioactive agents. The molecular weight of the pseudo-oligomeric conjugated drug may be between 200 and 60,000 Da, or larger. Pseudo-oligomeric conjugated drug 610 may have solubility in water less than that of the bioactive agent. Pseudo-oligomeric conjugated drug 610 may include multiple monomers of the same bioactive agent connected by pseudo-oligomeric interlinking groups 614, 618. Each pseudo-oligomeric interlinking group may serve as a pseudo-oligomeric interlinking agent by enabling the linking of two monomers.

The pseudo-oligomeric conjugated drug may be formed by providing at least three molecules of a hydroxylic or di-hydroxylic bioactive agent, and mixing them with at least two molecules of a pseudo-oligomeric interlinking group in a solution. A pseudo-oligomerization catalyst may be added to the solution. The solution may be heated to a pseudo-oligomeric reaction temperature, thereby forming a pseudo-oligomeric conjugated drug where a molecule of the bioactive agent may be connected to a molecule of the bioactive agent by a molecule of the pseudo-oligomeric interlinking group, and a third molecule of the bioactive agent may be connected to either of the first two molecules of the bioactive agent by a second molecule of the pseudo-oligomeric interlinking group. The pseudo-oligomerization reaction temperature may be between 25 and 140 degrees centigrade.

After the deployment of stent 120, 220, pseudo-oligomeric conjugated drug 610 may eventually separate into bioactive agent 622, pseudo-oligomeric interlinking group 624, and an intermediate pseudo-oligomeric sequence consisting of bioactive agent 626, pseudo-oligomeric interlinking group 628, and bioactive agent 630, allowing bioactive agent 622 to perform its intended pharmaceutical function, while pseudo-oligomeric interlinking group 624 and the intermediate pseudo-oligomeric sequence may be retained within polymeric coating 122, 222. Alternatively, pseudo-oligomeric interlinking group 624 may diffuse from polymeric coating 122, 222 and expelled from the body or further degraded then expelled, or may be absorbed by the body in some pharmacologically benign form. Alternatively, bioactive agent 622 may provide bioavailability upon elution from stent 120, 220 without requiring separation from pseudo-oligomeric interlinking group 624. As time progresses, bioactive agents 626, 630 may be eluted from polymeric coating 122, 222 as the intermediate pseudo-oligomeric sequence further disassociates.

Another aspect of the present invention entails modification of slightly or moderately soluble hydroxyl- and lactone-bearing drugs to increase their molecular weight, decrease their water solubility, and lower their rate of diffusion through a thin stent coating or their erosion into a biological environment. The lipophilic conjugated drug may be used in a highly controlled-release coating system for the precise delivery, for example, of antiproliferative drugs around endovascular stents to prevent vascular restenosis without impairing the pharmacological effects of the drugs. A lipophilic conjugated drug or a polymeric matrix with an interdispersed lipophilic conjugated drug may be used to coat the stent.

Figure 7:
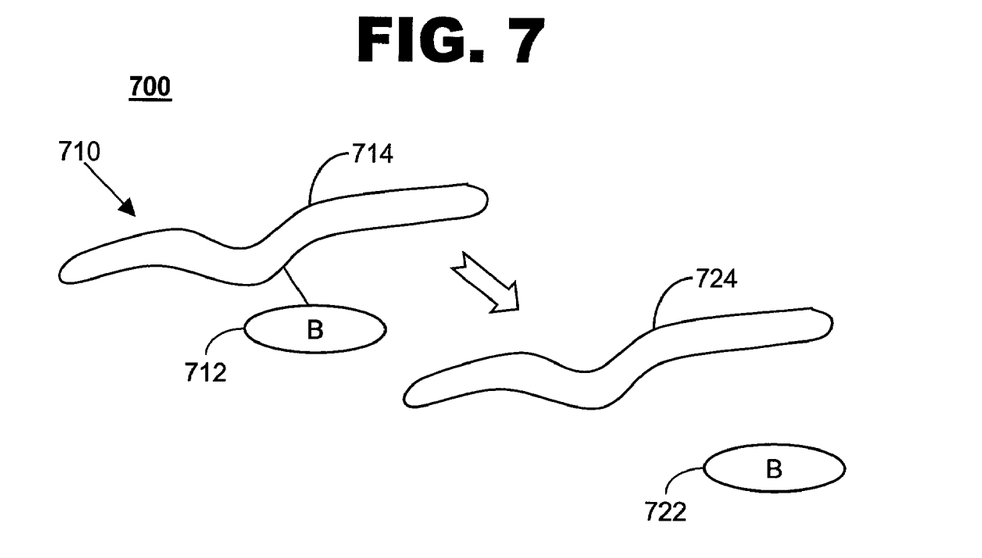
FIG. 7 is a schematic diagram of a lipophilic conjugated drug and its timed-release mechanism, in accordance with the current invention.

FIG. 7 shows a schematic diagram of a lipophilic conjugated drug and its timed-release mechanism, in accordance with the present invention at 700. Lipophilic conjugated drug 710 may include a bioactive agent 712 and a control agent 714. Bioactive agent 712 of lipophilic conjugated drug 710 may include a 15 lipophilic drug derivative of a lipophilic drug, where lipophilic conjugated drug 710 may have a molecular weight greater than that of the lipophilic drug derivative. The lipophilic drug may be, for example, an antiproliferative. The lipophilic drug derivative may include a non-pharmacologically critical hydroxyl group. The control agent, such as an acid chloride, may be attached to the non-pharmacologically critical hydroxyl group. The lipophilic drug may be podophyllotoxin. The control agent may be derived from an acid anhydride of a fatty acid with between three and twenty carbon atoms. The acid anhydride may include a stearic acid anhydride.

The lipophilic drug derivative may include a non-pharmacologically critical lactone. The lactone may be opened up to attach a non-pharmacologically critical control agent. The lipophilic drug may include podophyllotoxin and the control agent may include a long-chain fatty acid, containing between three and twenty carbon atoms.

The lipophilic conjugated drug may be formed by providing a bioactive agent with a non-pharmacologically critical hydroxyl group, and mixing the bioactive agent with an acid chloride in a solution. The solution may be heated to a lipophilic reaction temperature, thereby forming the lipophilic conjugated drug. The bioactive agent may be podophyllotoxin. The lipophilic reaction temperature may be between 25 and 140 degrees centigrade.

A lipophilic conjugated drug may also be formed by providing a bioactive agent with a non-pharmacologically critical hydroxyl group, and mixing the bioactive agent with an acid anhydride of a fatty acid including between three and twenty carbon atoms in a solution. The solution may be heated to a lipophilic reaction temperature to form the lipophilic conjugated drug. The lipophilic reaction temperature may be between 25 and 140 degrees centigrade.

A lipophilic conjugated drug may also be formed by providing a bioactive agent with a non-pharmacologically critical lactone, and mixing the bioactive agent with a long-chain fatty alcohol including between three and twenty carbon molecules in a solution. A lipophilic catalyst may be added to the solution. The solution may be heated to a lipophilic reaction temperature to form the lipophilic conjugated drug. The bioactive agent may be podophyllotoxin. The lipophilic catalyst may be an organometallic transesterification catalyst. The lipophilic reaction temperature may be between 25 and 140 degrees centigrade.

After the deployment of stent 120, 220, lipophilic conjugated drug 710 may separate in due time into bioactive agent 722 and control agent 724, allowing bioactive agent 722 to perform its intended pharmaceutical function, whereas control agent 724 may be retained within polymeric coating 122, 222, or may be leeched from polymeric coating 122, 222 and metabolized, adsorbed, biodegraded, or expelled from the body. Alternatively, bioactive agent 722 may provide bioavailability upon elution from stent 120, 220 without requiring separation from control agent 724.

Another aspect of the current invention is a drug-polymer coated stent. The drug-polymer coated stent may include a cardiovascular stent with a stent framework and a polymeric coating on the stent framework. The polymeric coating may include a biocompatible polymer comprising a conjugated drug, where the elution rate of the interdispersed drug may be predetermined. The polymeric coating may contain a polymeric matrix in which one or more conjugated drugs may be interdispersed.

Figure 8:
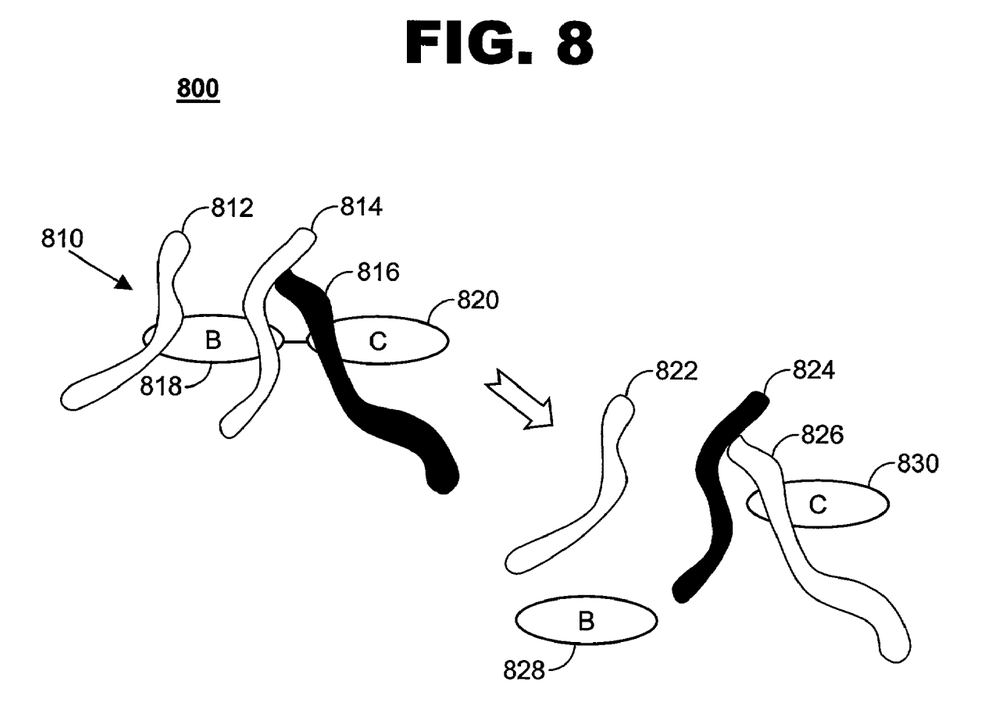
FIG. 8 is a schematic diagram of a conjugated drug dispersed within a polymer matrix and its timed-release mechanism, in accordance with the current invention.

FIG. 8 shows a schematic diagram of a conjugated drug interdispersed within a polymeric matrix and its timed-release mechanism, in accordance with the present invention at 800. Drug-polymer coating 810 may include polymer chains 812, 814, 816 and one or more conjugated drugs including bioactive agent 818 and control agent 820. Drug-polymer coating 810 may include one or more of linear, branched, or networked polymer chains. Polymer chains 812, 814, 816 may form a polymeric matrix. The polymeric matrix may include, for example, a caprolactone polymer, or a caprolactone copolymer. The conjugated drug consisting of bioactive agent 818 and control agent 820 may be interdispersed throughout drug-polymer coating 810. After the deployment of stent 120, 220, bioactive agent 828 may have separated from control agent 830 and diffused out from drug-polymer coating 810, leaving the polymeric matrix including polymer chains 822, 824, 826 behind. Alternatively, the conjugated drug may diffuse out from the coating and then disassociate into bioactive agent 828 and control agent 830. Alternatively, bioactive agent 828 may express full bioavailability after diffusion from the coating without separating from the control agent. Alternatively, polymer chains 822, 824, 826 may become soft, fragmentize, or be absorbed into the body to provide bioavailability for the conjugated drug in a process referred to as bulk erosion. The bioactive agents may be released by a combination of these mechanisms and variants on them.

Another aspect of the present invention is a method of manufacturing a drug-polymer coated stent.

Figure 9:
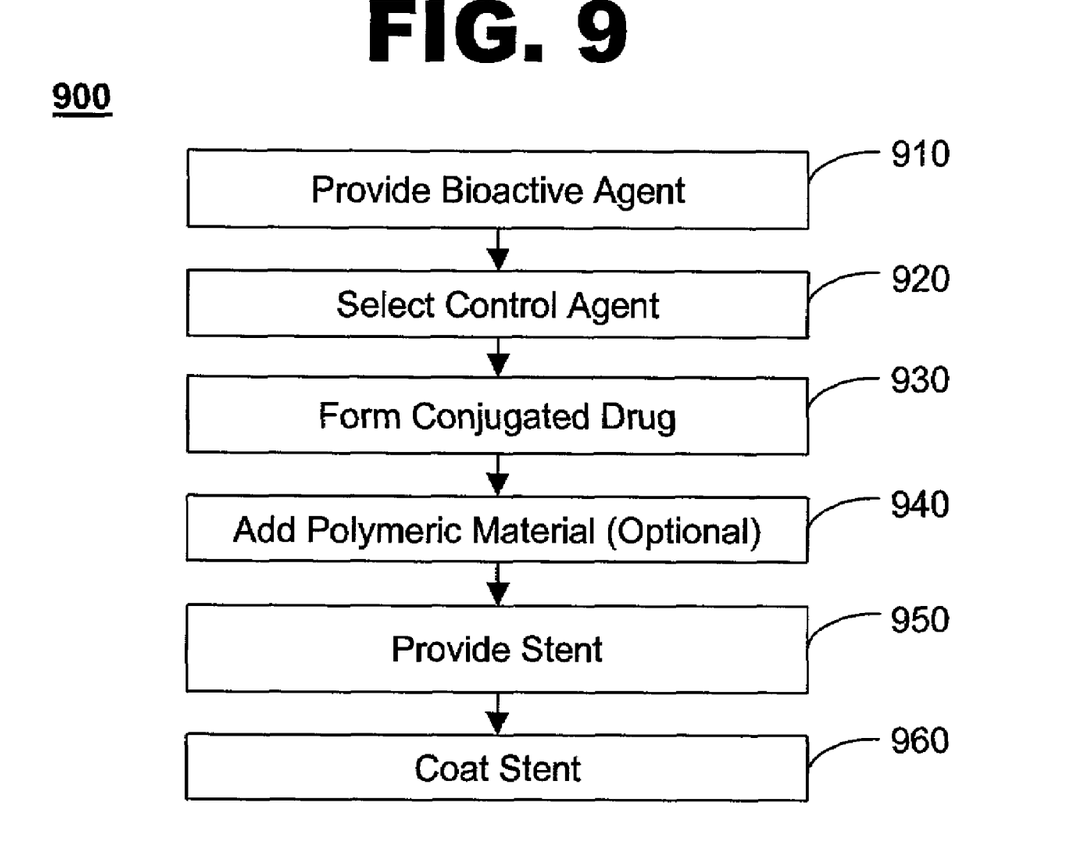
FIG. 9 is a flow diagram of one embodiment of a method for manufacturing a conjugated drug-polymer coated stent, in accordance with the current invention.

FIG. 9 shows a flow diagram of one embodiment of a method for manufacturing a conjugated drug-polymer coated stent, in accordance with the present invention at 900. Drug-polymer coated stent manufacturing method 900 may comprise various steps in the manufacture of a drug-polymer coated stent. The drug-polymer coated stent may be manufactured by providing a bioactive agent, as seen at block 910. A suitable control agent may be selected to provide bioavailability of the bioactive agent at a predetermined elution rate, as seen at block 920. A conjugated drug may be formed with the bioactive agent and the control agent in a manner such that the elution rate of the bioactive agent from the stent coating meets the predetermined elution rate, as seen at block 930. A conjugated drug may be formed from a bioactive agent and a control agent, using any of the aforementioned methods or any suitable method for forming the conjugated drug. The conjugated drug may be selected from a covalently-linked conjugated drug, a pseudodimeric conjugated drug, a pseudo-oligomeric conjugated drug, a lipophilic conjugated drug, or any combination thereof.

The method of manufacturing a drug-polymer coated stent may also include mixing a polymer coating material with the conjugated drug prior to coating the stent framework, as seen at block 940. The polymer coating material may include, for example, polycaprolactone, a caprolactone copolymer, a synthetic polymer, a naturally occurring polymer, a non-synthetic polymer derivative, or any suitable polymer coating material. The additional polymeric material may result in a polymeric matrix in which the conjugated drug may be interdispersed. One or more non-modified drugs or bioactive agents also may be included in the polymer coating. A stent or stent framework may be provided, as seen at block 950. The stent framework may then be coated with the conjugated drug and optional polymeric matrix using any suitable method such as spraying, dipping or painting, as seen at block 960. The coating may be dried, if necessary, to remove any solvent or water used in the conjugated drug formation or coating process.

Another aspect of the present invention is a method for treating vascular conditions, including inserting a stent within a vessel in a body, separating at least a portion of a polymeric coating on the stent into a bioactive agent and a control agent, and eluting the bioactive agent. The control agent may control the elution rate of the bioactive agent. The control agent may be selected based on a specified or predetermined elution rate of the bioactive agent.

Another aspect of the present invention is a system for treating vascular conditions, including a means for inserting a stent within a vessel in the body, a means for allowing separation of at least a portion of a polymeric coating on the stent into a bioactive agent and a control agent, and a means for eluting the bioactive agent. A means for inserting the stent within a vessel in the body may include a catheter for stent delivery, and a balloon for stent deployment. Alternatively, the stent may be a self-expanding type, which may be deployed by removing a sheath from the stent to allow expansion of the stent.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A system for treating a vascular condition, comprising:
   a catheter;
   a stent coupled to the catheter; and
   a polymeric coating on the stent comprising a polymer mixed with at least one conjugated drug, wherein each conjugated drug includes a control agent and a bioactive agent, wherein the control agent controls an elution rate of the bioactive agent,
   wherein the conjugated drug comprises a pseudodimer of the bioactive agent, wherein the pseudodimer has a molecular weight of at least twice that of the bioactive agent, the pseudodimer comprising a first bioactive agent and a second bioactive agent connected by a pseudodimeric interlinking group and wherein the first bioactive agent is a first molecule of podophyllotoxin, the second bioactive agent is a second molecule of podophyllotoxin, and the pseudodimeric interlinking group comprises an oxalate bridge, wherein the control agent is chosen from a group consisting of an acid chloride, an acid anhydride of fatty acid and a long chain fatty acid having between 3 and 20 carbon atoms.

2. A system for treating a vascular condition, comprising:
a catheter;
a stent coupled to the catheter; and
a polymeric coating on the stent comprising a polymer mixed with at least one conjugated drug, wherein each conjugated drug includes a control agent and a bioactive agent, wherein the control agent controls an elution rate of the bioactive agent,
wherein the conjugated drug comprises a pseudodimer of the bioactive agent, the pseudodimer has a molecular weight of at least twice that of the bioactive agent, the pseudodimer comprising a first bioactive agent and a second bioactive agent connected by a pseudodimeric interlinking group, wherein the first bioactive agent is a first molecule of podophyllotoxin, the second bioactive agent is a second molecule of podophyllotoxin, and the pseudodimeric interlinking group comprises a carbonate bridge
wherein the control agent is chosen from a group consisting of an acid chloride, an acid anhydride of fatty acid and a long chain fatty acid having between 3 and 20 carbon atoms.

3. A system for treating a vascular condition, comprising:
a catheter;
a stent coupled to the catheter; and
a polymeric coating on the stent comprising a polymer mixed with at least one conjugated drug, wherein each conjugated drug includes a control agent and a bioactive agent, wherein the control agent controls an elution rate of the bioactive agent,
wherein the bioactive agent comprises a podophyllotoxin, the podophyllotoxin containing a non-pharmacologically critical hydroxyl group,
wherein the conjugated drug has a molecular weight greater than that of the podophyllotoxin,
wherein the control agent is attached to the non-pharmacologically critical hydroxyl group and wherein the control agent comprises an acid chloride.

4. A system for treating a vascular condition, comprising:
a catheter;
a stent coupled to the catheter; and
a polymeric coating on the stent comprising a polymer mixed with at least one conjugated drug, wherein each conjugated drug includes a control agent and a bioactive agent, wherein the control agent controls an elution rate of the bioactive agent,
wherein the bioactive agent comprises a lipophilic drug, the lipophilic drug containing a non-pharmacologically critical hydroxyl group,
wherein the conjugated drug has a molecular weight greater than that of the lipophilic drug,
wherein the control agent is attached to the non-pharmacologically critical hydroxyl group, and
wherein the lipophilic drug is podophyllotoxin and the control agent comprises an acid anhydride of a fatty acid with between three and twenty carbon atoms.

5. The system of claim 4 wherein the acid anhydride is a stearic acid anhydride.

6. A system for treating a vascular condition, comprising:
a catheter;
a stent coupled to the catheter; and
a polymeric coating on the stent comprising a polymer mixed with at least one conjugated drug, wherein each conjugated drug includes a control agent and a bioactive agent, wherein the control agent controls an elution rate of the bioactive agent,
wherein the bioactive agent comprises a lipophilic drug, the lipophilic drug containing a non-pharmacologically critical lactone,
wherein the conjugated drug has a molecular weight greater than that of the lipophilic drug, and
wherein the lipophilic drug is podophyllotoxin and the control agent comprises a long-chain fatty acid with between three and twenty carbon atoms.

7. A method of manufacturing a drug-polymer coated stent, comprising:
providing a stent framework;
forming a conjugated drug, wherein the conjugated drug comprises a bioactive agent and a control agent;
mixing the conjugated drug with a polymer; and
coating the stent framework with the conjugated drug and polymer mixture, wherein forming the conjugated drug comprises:
mixing the bioactive agent and at least one monomer in a solution;
adding a catalyst to the solution; and
forming a covalently-linked conjugated drug, wherein an absorbable polyester chain is linked to the bioactive agent, and the bioactive agent serves as a chain initiator,
wherein the bioactive agent is podophyllotoxin, the at least one monomer is a mixture of e-caprolactone and glycolide, and the catalyst is stannous octoate,
wherein the control agent is chosen from a group consisting of an acid chloride, an acid anhydride of fatty acid and a long chain fatty acid having between 3 and 20 carbon atoms.

8. A method of manufacturing a drug-polymer coated stent, comprising:
providing a stent framework;
forming a conjugated drug, wherein the conjugated drug comprises a bioactive agent and a control agent;
mixing the conjugated drug with a polymer; and
coating the stent framework with the conjugated drug and polymer mixture, wherein forming the conjugated drug comprises:
mixing the bioactive agent and at least one monomer in a solution;
adding a catalyst to the solution; and
forming a covalently-linked conjugated drug, wherein an absorbable polyester chain is linked to the bioactive agent, and the bioactive agent serves as a chain initiator,
wherein the bioactive agent is podophyllotoxin, the at least one monomer is a mixture of e-caprolactone and glycolide, and the catalyst is a zinc dialkyl, wherein the control agent is chosen from a group consisting of an acid chloride, an acid anhydride of fatty acid and a long chain fatty acid having between 3 and 20 carbon atoms.

9. A method of manufacturing a drug-polymer coated stent, comprising:
providing a stent framework;
forming a conjugated drug, wherein the conjugated drug comprises a bioactive agent and a control agent;
mixing the conjugated drug with a polymer; and
coating the stent framework with the conjugated drug and polymer mixture, wherein forming the conjugated drug comprises:
providing at least two molecules of a hydroxylic bioactive agent;
mixing at least two molecules of the hydroxylic bioactive agent and at least one molecule of a pseudodimeric interlinking group in a solution;
adding a pseudodimerization catalyst to the solution;
heating the solution to a pseudodimeric reaction temperature; and forming a pseudodimeric conjugated drug wherein a first molecule of the bioactive agent is connected to a second molecule of the bioactive agent by a molecule of the pseudodimeric interlinking group, wherein the control agent is chosen from a group consisting of an acid chloride, an acid anhydride of fatty acid and a long chain fatty acid having between 3 and 20 carbon atoms;

and wherein the hydroxylic bioactive agent is podophyllotoxin.

10. The method of claim 9 wherein the pseudodimeric interlinking group comprises diethyl oxalate.

11. The method of claim 9 wherein the pseudodimeric interlinking group comprises di-isopropyl carbonate.

12. The method of claim 9 wherein the pseudodimerization catalyst comprises an organometallic transesterification catalyst.

13. The method of claim 9 wherein the solution comprises a non-reactive solvent.

14. The method of claim 9 wherein the pseudodimerization reaction temperature is between 25 degrees centigrade and 140 degrees centigrade.

15. A method of manufacturing a drug-polymer coated stent, comprising:

providing a stent framework;

forming a conjugated drug, wherein the conjugated drug comprises a bioactive agent and a control agent;

mixing the conjugated drug with a polymer; and coating the stent framework with the conjugated drug and polymer mixture, wherein forming the conjugated drug comprises:

providing at least three molecules of a hydroxylic bioactive agent;

mixing at least three molecules of the hydroxylic bioactive agent and at least two molecules of a pseudo-oligomeric interlinking group in a solution;

adding a pseudo-oligomerization catalyst to the solution;

heating the solution to a pseudo-oligomeric reaction temperature; and forming a pseudo-oligomeric conjugated drug wherein a first molecule of the bioactive agent is connected to a second molecule of the bioactive agent by a first molecule of the pseudo-oligomeric interlinking group, and the second molecule of the bioactive agent is connected to a third molecule of the bioactive agent by a second molecule of the pseudo-oligomeric interlinking group, wherein the control agent is chosen from a group consisting of an acid chloride, an acid anhydride of fatty acid and a long chain fatty acid having between 3 and 20 carbon atoms;

and wherein the hydroxylic bioactive agent is podophyllotoxin.

16. The method of claim 15 wherein the pseudo-oligomerization reaction temperature is between 25 degrees centigrade and 140 degrees centigrade.

17. A method of manufacturing a drug-polymer coated stent, comprising:

providing a stent framework;

forming a conjugated drug, wherein the conjugated drug comprises a bioactive agent and a control agent;

mixing the conjugated drug with a polymer; and coating the stent framework with the conjugated drug and polymer mixture, wherein forming the conjugated drug comprises:

providing a bioactive agent with a non-pharmacologically critical hydroxyl group;

mixing the bioactive agent with an acid chloride in a solution;

heating the solution to a lipophilic reaction temperature; and forming a lipophilic conjugated drug, wherein the control agent is chosen from a group consisting of an acid chloride, an acid anhydride of fatty acid and a long chain fatty acid having between 3 and 20 carbon atoms;

and wherein the bioactive agent is podophyllotoxin.

18. The method of claim 17 wherein the lipophilic reaction temperature is between 25 degrees centigrade and 140 degrees centigrade.

19. A method of manufacturing a drug-polymer coated stent, comprising:

providing a stent framework;

forming a conjugated drug, wherein the conjugated drug comprises a bioactive agent and a control agent;

mixing the conjugated drug with a polymer; and coating the stent framework with the conjugated drug and polymer mixture, wherein forming the conjugated drug comprises:

providing a bioactive agent with a non-pharmacologically critical hydroxyl group;

mixing the bioactive agent with an acid anhydride of a fatty acid comprising between three and twenty carbon atoms in a solution;

heating the solution to a lipophilic reaction temperature; and forming a lipophilic conjugated drug, wherein the control agent is chosen from a group consisting of an acid chloride, an acid anhydride of fatty acid and a long chain fatty acid having between 3 and 20 carbon atoms;

and wherein the bioactive agent is podophyllotoxin.

20. The method of claim 19 wherein the lipophilic reaction temperature is between 25 degrees centigrade and 140 degrees centigrade.

21. A method of manufacturing a drug-polymer coated stent, comprising:

providing a stent framework;

forming a conjugated drug, wherein the conjugated drug comprises a bioactive agent and a control agent;

mixing the conjugated drug with a polymer; and coating the stent framework with the conjugated drug and polymer mixture, wherein forming the conjugated drug comprises:

providing a bioactive agent with a non-pharmacologically critical lactone;

mixing the bioactive agent with a long-chain fatty alcohol comprising between three and twenty carbon atoms in a solution;

adding a lipophilic catalyst to the solution;

heating the solution to a lipophilic reaction temperature; and forming a lipophilic conjugated drug, wherein the control agent is chosen from a group consisting of an acid chloride, an acid anhydride of fatty acid and a long chain fatty acid having between 3 and 20 carbon atoms;

and wherein the bioactive agent is podophyllotoxin.

22. The method of claim 21 wherein the lipophilic catalyst is an organometallic transesterification catalyst.

23. The method of claim 21 wherein the lipophilic reaction temperature is between 25 degrees centigrade and 140 degrees centigrade.

* * * * *